United States Patent
Mann

(10) Patent No.: US 10,341,760 B2
(45) Date of Patent: Jul. 2, 2019

(54) ELECTRONIC EAR PROTECTION DEVICES

(71) Applicant: IP Holdings, Inc., Grand Prairie, TX (US)

(72) Inventor: Doug Mann, Carlsbad, CA (US)

(73) Assignee: IP Holdings, Inc., Grand Prairie, TX (US)

( * ) Notice: Subject to any disclaimer, the term of this patent is extended or adjusted under 35 U.S.C. 154(b) by 0 days.

(21) Appl. No.: 15/910,640

(22) Filed: Mar. 2, 2018

(65) Prior Publication Data
US 2018/0338201 A1 Nov. 22, 2018

Related U.S. Application Data

(60) Provisional application No. 62/509,567, filed on May 22, 2017.

(51) Int. Cl.
*A61F 11/06* (2006.01)
*H04R 1/10* (2006.01)
*H04R 3/04* (2006.01)

(52) U.S. Cl.
CPC ......... *H04R 1/1083* (2013.01); *H04R 1/1041* (2013.01); *H04R 3/04* (2013.01); *H04R 1/105* (2013.01); *H04R 1/1008* (2013.01); *H04R 2430/01* (2013.01)

(58) Field of Classification Search
CPC .. H04R 1/1083; H04R 1/1008; H04R 1/1041; H04R 1/105
See application file for complete search history.

(56) References Cited

U.S. PATENT DOCUMENTS

| | | |
|---|---|---|
| 3,394,226 A | 7/1968 | Andrews, Jr. |
| 3,952,158 A | 4/1976 | Kyle et al. |
| 4,006,318 A | 2/1977 | Sebesta et al. |
| 4,677,678 A | 6/1987 | McCutchen |
| 5,426,719 A | 6/1995 | Franks et al. |
| 5,815,582 A | 9/1998 | Claybaugh et al. |
| 8,229,740 B2 | 7/2012 | Nordholm et al. |
| 8,243,943 B2 | 8/2012 | Nordin et al. |
| 8,611,554 B2 | 12/2013 | Short et al. |
| 9,154,867 B2 | 10/2015 | Jenkins |
| 2017/0048609 A1* | 2/2017 | Schnell ............... H04R 1/1083 |
| 2017/0142511 A1* | 5/2017 | Dennis ................ H04R 1/1083 |
| 2017/0264988 A1* | 9/2017 | Stringer ............... H04R 1/1041 |

* cited by examiner

*Primary Examiner* — Simon King
(74) *Attorney, Agent, or Firm* — Knobbe, Martens, Olson & Bear, LLP

(57) ABSTRACT

Electronic ear protection devices are provided herein. In accordance with one aspect of the invention, an electronic ear protection device comprises a pair of ear cups, each comprising a speaker, and a headband that interconnects and supports the pair of ear cups on opposite ends of the headband. The device also includes an electronic sound control module disposed outside of the ear cups. The module comprises one or more microphones configured to detect an ambient sound, and one or more inputs operable to control a volume of the ambient sound signal delivered to the speakers.

21 Claims, 13 Drawing Sheets

ELECTRONIC EAR PROTECTION DEVICES

CROSS-REFERENCE TO RELATED APPLICATIONS

This application claims the benefit of U.S. Provisional Application No. 62/509,567, filed May 22, 2017 and titled ELECTRONIC EAR PROTECTION DEVICES, the entire contents of which are hereby incorporated by reference and should be considered a part of this specification.

BACKGROUND

Field

The described technology generally relates to electronic ear protection devices.

Description of the Related Art

Electronic ear protection devices can be used for a variety of purposes. For example, headsets can be used to protect a user's ears from damage in loud environments.

SUMMARY

There is a need for an ear protection device that can protect a user's ears from damage in loud environments, while allowing a user to hear certain sounds. An electronic ear protection device can allow a user to hear an ambient sound source captured via microphone(s).

The electronic ear protection device can be used in a wide variety of applications. In one example, the device can protect a user from noises in loud places like shooting ranges. At the same time, the device can allow the user to allow hear ambient sounds such as a voice from a person nearby.

In accordance with one aspect of the invention, an electronic ear protection device is provided. The device comprises a pair of ear cups, each comprising a speaker, and a headband that interconnects and supports the pair of ear cups on opposite ends of the headband. The device also includes an electronic sound control module disposed outside of the ear cups.

By disposing the sound control module outside of the ear cups, the ear cups can be designed to have zero or a minimum number of exposed holes, openings, or cavities, such that ear cups may better isolate ears of the user of the device from loud environment. For instance, this can advantageously increase the noise reduction rating (NRR) of the headset or ear protection device as compared with other headset designs that include more recesses, cavities or holes in the ear cups.

The module includes: one or more microphones configured to detect an ambient sound and generate a corresponding ambient sound signal; one or more user interfaces actuatable by a user to control a volume of the ambient sound signal delivered to the speakers in the ear cups (e.g. one or more buttons); and circuitry configured to process the ambient sound signal and to communicate the processed ambient sound signal to the speakers in the ear cups. The circuitry can be further configured to filter out or compress audio above a threshold decibel level and/or provide frequency-dependent amplification to at least the ambient sound signal.

The electronic sound control module may be coupled to at least one end of the headband and electrically connected to the speakers in the ear cups via a connector between the headband and the ear cups, or may be coupled to an outer surface of at least one of the pair of ear cups. Said pair of ear cups may include outer shells without any openings therein.

The electronic sound control module may comprises a first unit attached to a first end of the headband and a second unit attached to a second end of the headband opposite the first end of the headband, wherein the first unit includes the one or more inputs. The second unit may comprise one or more batteries housed therein.

The one or more microphone may comprise a first microphone operable to capture ambient sound from a first direction, and a second microphone configured to capture ambient sound from a second direction different from the first direction. The circuitry may be further configured to control sound output to the speaker of one of the pair or ear cups based on ambient sound captured by the first microphone and to separately control sound output to the speaker of the other of the pair of ear cups based on ambient sound captured by the second microphone.

In accordance with another aspect of the invention, an electronic ear protection device is provided. The device comprises a pair of ear cups, each having a speaker therein; a headband positioned above the pair or ear cups; and a pair of arms that connect the pair of ear cups to opposite ends of the headband; and an electronic sound control module attached to the headband, the module comprising one or more microphones configured to detect an ambient sound and generate a corresponding ambient sound signal, one or more inputs operable to control a volume of the ambient sound signal delivered to the speakers in the ear cups via one or more cables that extend from the electronic sound control module to the speakers, and circuitry operable to process the ambient sound signal and to communicate the processed ambient sound signal to the speakers in the ear cups via the one or more cables, wherein a user can actuate the one or more inputs of the electronic sound control module attached to the headband to thereby control the volume of ambient sound provided to the user through the speakers in the ear cups.

The circuitry may be configured to provide different amounts of amplification to certain frequencies relative to other frequencies when processing the ambient sound signal and/or filter out the ambient sound signal having a decibel level greater than a predetermined decibel level. The one or more inputs may comprise one or more buttons. A user may be able to actuate the one or more inputs to thereby turn the power of the circuitry on or off.

The electronic sound control module may comprise a first unit attached to a first end of the headband and a second unit attached to a second end of the headband opposite the first end of the headband, wherein the first unit includes the one or more inputs. The second unit may comprise one or more batteries housed therein. The first unit may comprise a first microphone operable to detect the ambient sound from a first direction, and the second unit may comprise a second microphone operable to detect the ambient sound from a second direction different from the first direction. The circuitry may be configured to control sound output to the speaker of one of the pair or ear cups based on ambient sound captured by the first microphone and to separately control sound output to the speaker of the other of the pair of ear cups based on ambient sound captured by the second microphone.

The electronic sound control module may further comprise an electronic sound control module housing, wherein the housing houses the circuitry and the one or more microphones therein.

BRIEF DESCRIPTION OF THE DRAWINGS

Example implementations disclosed herein are illustrated in the accompanying schematic drawings, which are for illustrative purposes only.

DETAILED DESCRIPTION

Figure 1:
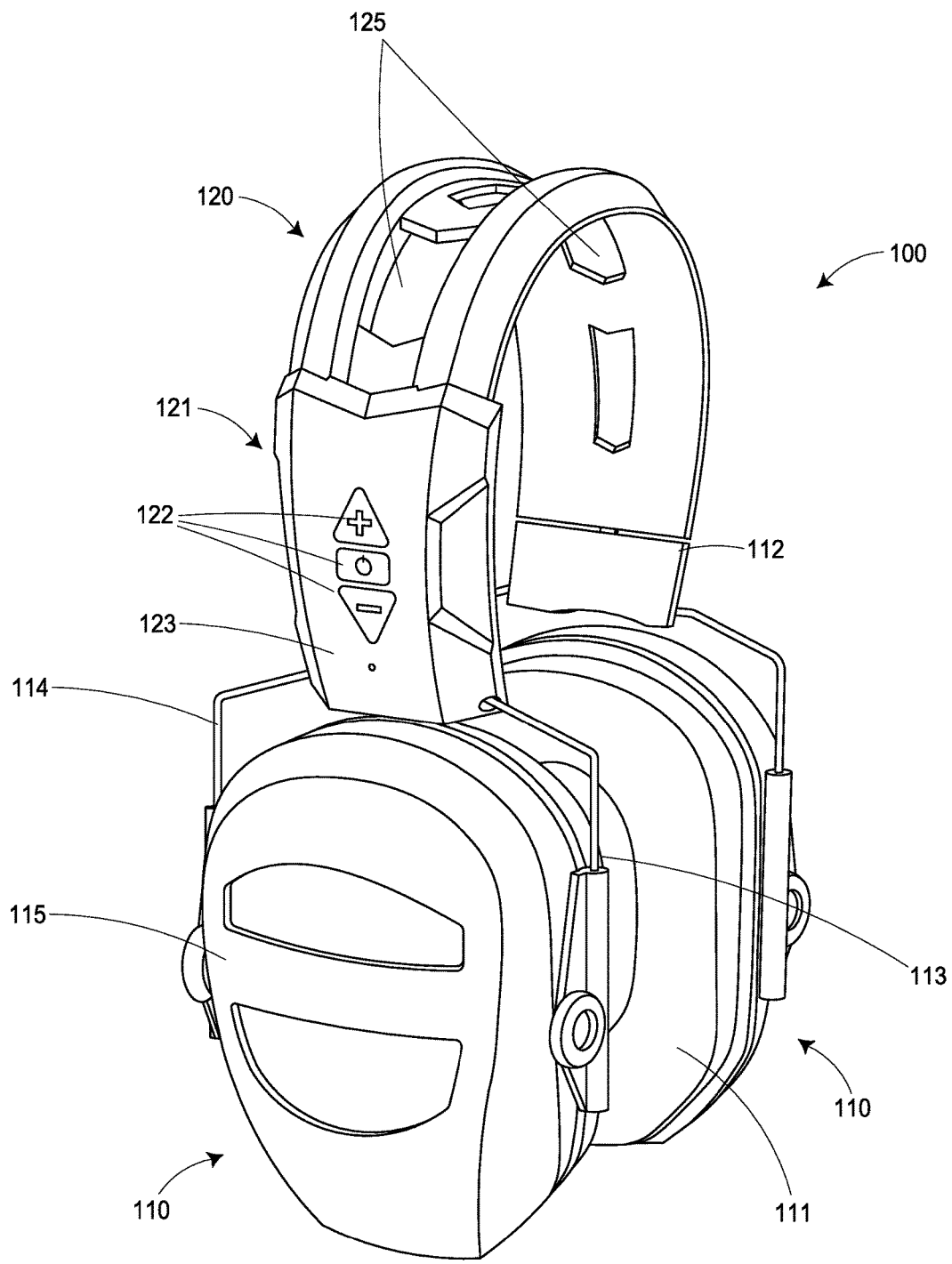
FIG. 1 is a perspective view of an electronic ear protection device according to one embodiment.

The following detailed description is directed to certain implementations for the purposes of describing the innovative aspects. However, the teachings herein can be applied in a multitude of different ways. As will be apparent from the following description, an audio amplification and ear protection device can be implemented in a wide variety of form factors (e.g., on-ear or over-ear cups/muffs) and can include a wide range of features and functionality.

Apparatus and methods for electronic ear protection devices are provided herein. The electronic ear protection device can protect the user's ears from damage by limiting the volume of loud sounds. In certain configurations, an electronic ear protection device includes at least one microphone that captures ambient sound from an ambient audio source and the device can be implemented to provide attenuation or compression of sounds of large amplitude, and thus, serves as an ear protection device.

In certain implementations, an electrical system of a multi-source audio amplification and ear protection device includes variable gain amplification circuitry that operates with automatic gain control (AGC) to reduce the volume of ambient sounds after a loud event has been detected. In one example, after detecting a high volume ambient sound event, such as a gunshot, the device can operate with audio compression for a certain amount of time. Implementing the device in this manner helps attenuate the loudness of echoes of an initial loud event and/or other loud events occurring within a certain time frame thereafter. For instance, the user may be in a hunting party and the compression mode can be triggered after an initial gunshot is fired toward a discovered prey. Without requiring the user to manually control the volume, automatic gain control can decrease the volume of echoes of the initial gunshot, as well as to decrease the loudness of subsequent gunshots fired at the discovered prey from the user and/or other members of the hunting party. Although an example of a gunshot is provided, automatic gain control can provide gain compression to a wide variety of loud noises, including, for instance, crashing steel, passing race cars or motorcycles, fireworks, concerts, etc.

In certain implementations, the electronic ear protection device can provide frequency dependent amplification to ambient sound, thereby providing different amounts of amplification to certain frequencies relative to other frequencies. For instance, the device can provide different amounts of gain to sounds in different frequency ranges, such as a high frequency range relative to a low frequency range. In one example, the device can provide a relatively large amount of attenuation to low frequency sounds associated with boat motors, while providing a relatively large amount of amplification to frequencies associated with human voice. Thus, a user of the device can hear a boat engine at a reduced or attenuated volume, while hearing human voices (including, for instance, voices of passengers/observers, vehicle operators, and/or towed persons) at a relatively louder volume.

The sound output control can be provided in a wide variety of ways. In one example, the electronic circuitry can include analog amplifiers, such as variable and/or programmable gain amplifiers, used to provide a desired amount of amplification. In another example, the amplification is achieved at least in part by using digital processing. For instance, analog signals captured by the device's microphones can be converted into the digital domain using analog-to-digital converters. Thereafter, the values of the digital signals can be adjusted to provide digital amplification, and thereafter adjusted digital signals can be converted into signals suitable for driving the device's speakers. In addition to amplification, the device's electronic circuitry can also provide equalization, echo suppression or cancellation, compensation for multipath acoustic effects, noise cancellation, wind reduction, and/or other processing.

For example, in one embodiment, the device's electronic circuitry provides at least one of noise management, acoustic feedback control, delay filtering, or customized hearing loss compensation. The noise management can include, for example, spectral subtraction, binaural noise reduction, adaptive noise cancellation, directional microphone processing, impulsive sound suppression, wind noise reduction, automatic volume control, volume control learning, and/or low-level expansion. The customized hearing loss compensation can include, for example, adaptive dynamic range compensation (for instance, linear quasi-time-invariant compression) and/or wide dynamic range compensation (for instance, syllabic sub-band compression).

FIG. 1 illustrated an embodiment of an electronic ear protection device 100. The electronic ear protection device 100 includes ear cups 110 and a headband 120 that couples the ear cups 110 through connectors 114. The electronic ear protection device 100 may be worn by the user by putting the ear cups 110 on the user's ears, while putting the headband 120 over the head of the user so that the headband 120 sits on the top of the user's head. In one embodiment, the ear cups 110 can sit on the ear. In another embodiment, the ear cups 110 can sit over the ear, such that the ear is enclosed by the ear cup 110. The ear cups 110 may include outer shells 115 enclosing the ear cups 110, and pads 111 made of soft materials such as foam, to provide a greater amount of ear protection and/or improved comfort for extended periods of time. The ear cups 110 and their components may be designed such that the electronic ear protection device 100 may enclose the user's ears and significantly reduce the amount of ambient sound that directly reaches the user, such that the ear cups of the device may be even used as a passive device (e.g., exclude any electronics) suitable for a wide range of loud environments, including, but not limited to shooting ranges, construction sites, etc. For example, the outer shells 115 of the ear cups 110 may contain zero or a minimum number of exposed holes or openings such that ear cups 110 may isolate ears of the user of the device 100 from loud environment better, advantageously increasing the noise reduction rating (NRR) of the headset or ear protection device 100 as compared with other headset designs that include more recesses, cavities or holes in the ear cups 110.

In the illustrated embodiment, the headband 120 has openings 125, such that the user's head is exposed and vented through the openings, thus relieving possible discomfort on the user from prolonged use of the device, such as sweating. The headband 120 may contain smooth foam or other suitable soft materials for the comfort of the user of the device 100. In some embodiments, the width of the device 100 can be adjusted, for example, by retracting the ear cups 110 from the ends of the headband 120 via its junction 112 with ear cups 110.

The device 100 can be used to limit or attenuate loud sounds, thereby protecting a user's ears from damage. For example, the device 100 can be implemented to attenuate or compress audio sounds above a particular threshold, such as loud ambient sounds detected by the device's microphone(s). For instance, when the device 100 detects sound above a threshold level (for instance, 75 dB), the audio electronics of the device 100 can reduce the signal provided to the speaker of the corresponding ear such that the sound heard by the user's ear is within a safe volume level. In another embodiment, when electronics in the device 100 detect a sound about a predetermined threshold level (e.g., a gunshot at a shooting range), the audio electronics of the device 100 can filter out audio above the predetermined threshold, so that the user does not hear the higher decibel sound. In certain implementations, the device's threshold level(s) are user-adjustable.

In certain embodiments, the device 100 is implemented with automatic gain control to reduce the volume of ambient sounds after a loud event has been detected. Implementing the device in this manner helps attenuate the loudness of echoes of an initial loud event and/or other loud events occurring relatively soon thereafter. In certain implementations, the device's time window(s) and/or threshold level(s) for automatic compression are user-adjustable and/or vary with an operating mode or profile of the device. In certain embodiments, the device 100 provides frequency dependent amplification to ambient sound, thereby providing different amounts of amplification to certain frequencies relative to other frequencies.

The electronic ear protection device 100 may include an electrical system and/or an electrical circuitry as described below. In the illustrated embodiment, the electronics of the headset or ear protection device 100 are advantageously positioned in the headband 120, allowing the minimizing of recesses, cavities and/or holes in the ear cups 110 to thereby increase the noise reduction capability and rating of the headset 100 since the amount of material removed from the ear cups 110 is reduced (e.g., minimized). The headband 120 includes an electronic sound control module 121 which includes a microphone 123 and electronic circuitry for processing sounds detected from the microphone 123 and for driving speakers 113 within the ear cups 110, wherein the speaker 113 and the module 121 on the headband 120 may be electrically connected through wires within the one or more connectors or arms 114 that couple the ear cups 110 to the headband 120. The headband 120 may contain electrical wiring embedded therein to connect the module 121 and the speaker 113 in the ear cup 110 at the opposite side of the module 121. In the illustrated embodiment, the ear cups 110 may be electrically connected via a wire concealed in the headband 120 that extends through one or more of the connectors or arms 114. In some embodiment, the headset or ear protection device 100 may include a power source (e.g. one or more batteries), such as the battery 307 in FIG. 4. The internal power source may be located within the module 121, within/on the ear cups 110, on the headband 120, or anywhere else within the headset 100, and the power source may be connected to the electric circuitry, such as the sound processing unit 306 in FIG. 4, such that the power source provides electric power to the electric circuitry.

In the illustrate embodiment, the electronic sound control module 121 and the microphone 123 is located on the headband 120. In embodiments, the control module 121 and/or the microphone 123 may be located at any locations on the device 110. However, it would be understood by those skilled in the art that the location of the control module and the microphone may affect the acoustics and thus degree of the ear protection. For example, since the microphone needs exposure to the surrounding environment, a structure containing the microphone may require openings or holes exposed. Thus, designing the control module 121 and the microphone 123 as a separate structure from the ear cups 110 may enable more completely closed design of the ear cups.

Figure 2:
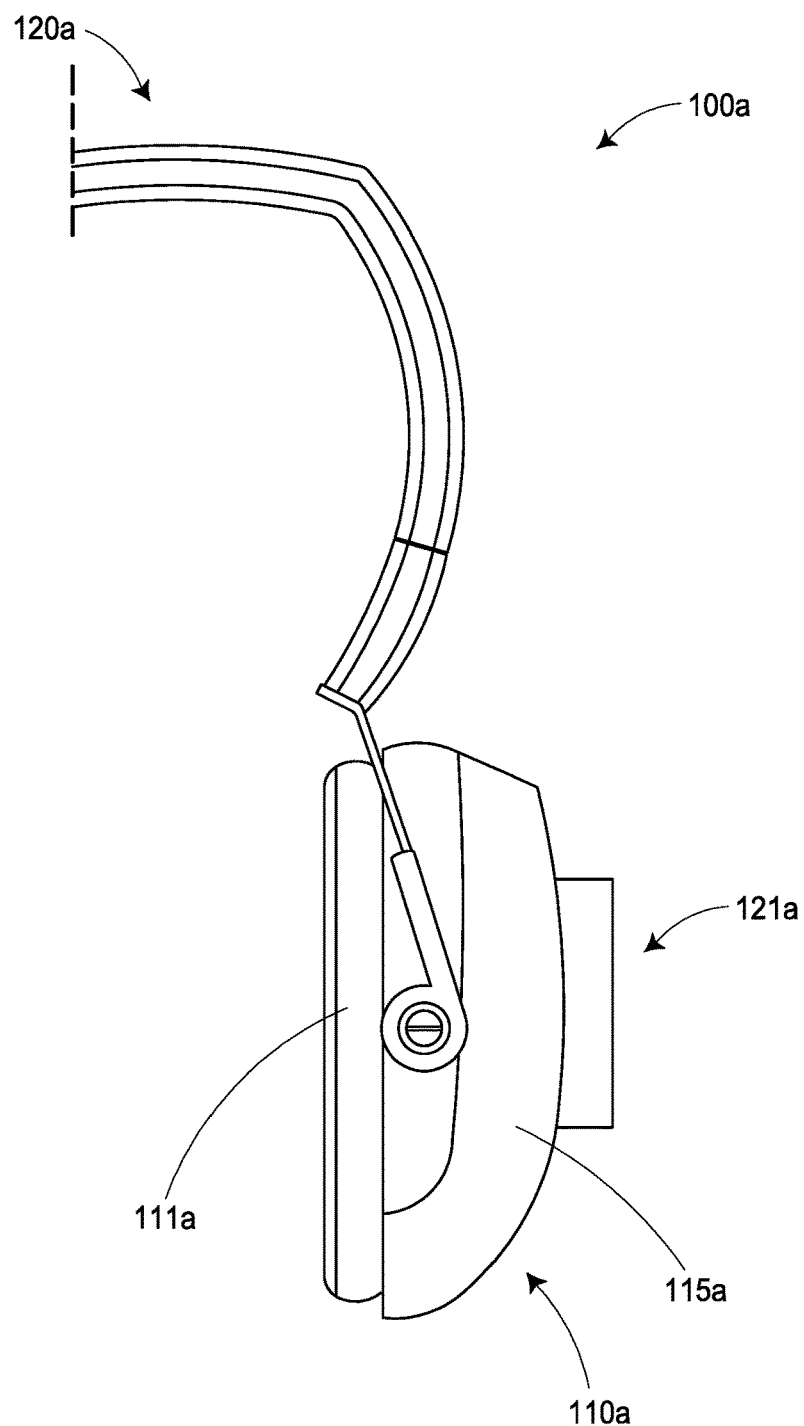
FIG. 2 is a partial schematic side view of an electronic ear protection device according to one embodiment.
Figure 3A:
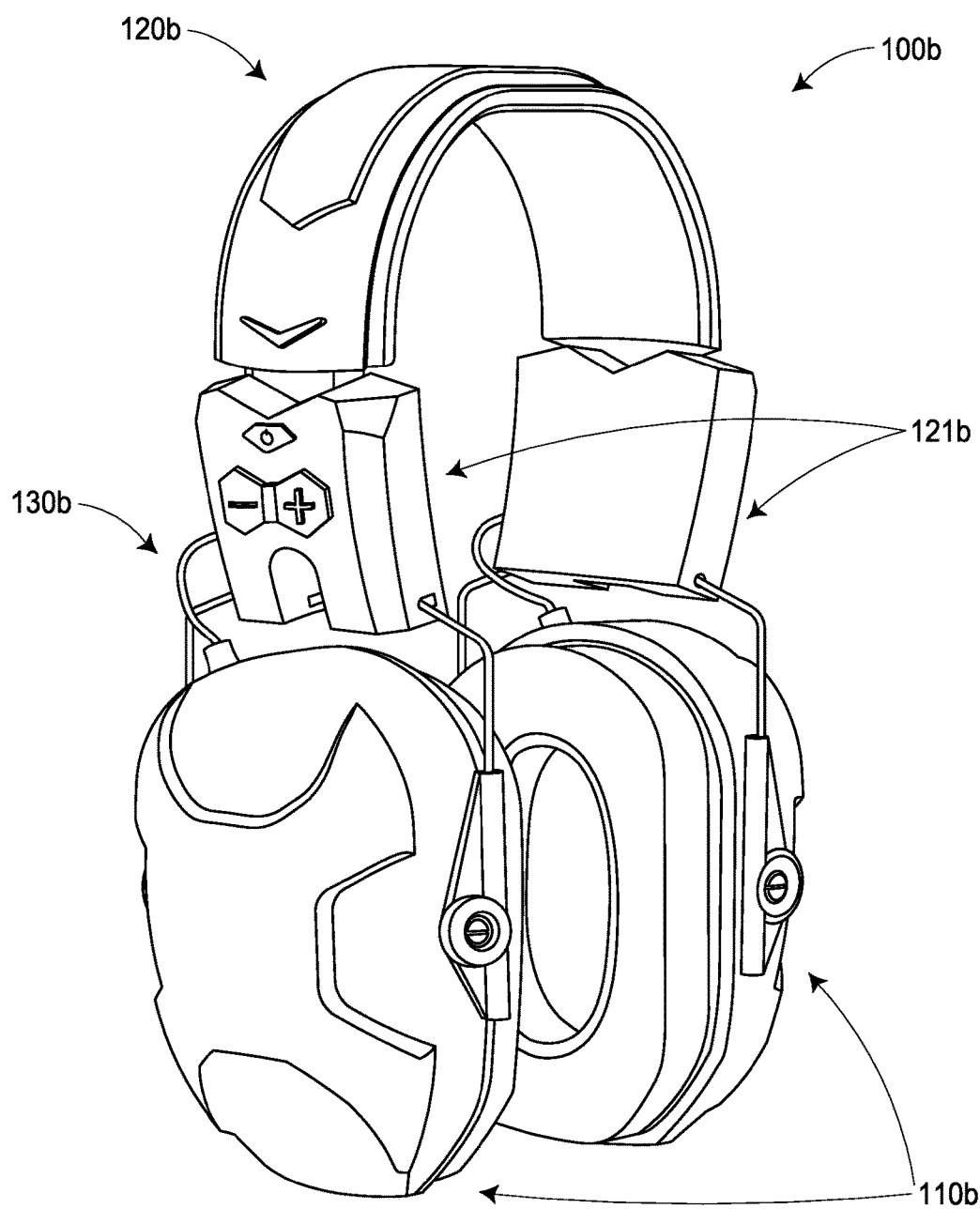
FIG. 3A is a perspective view of an electronic ear protection device according to one embodiment.
Figure 3B:
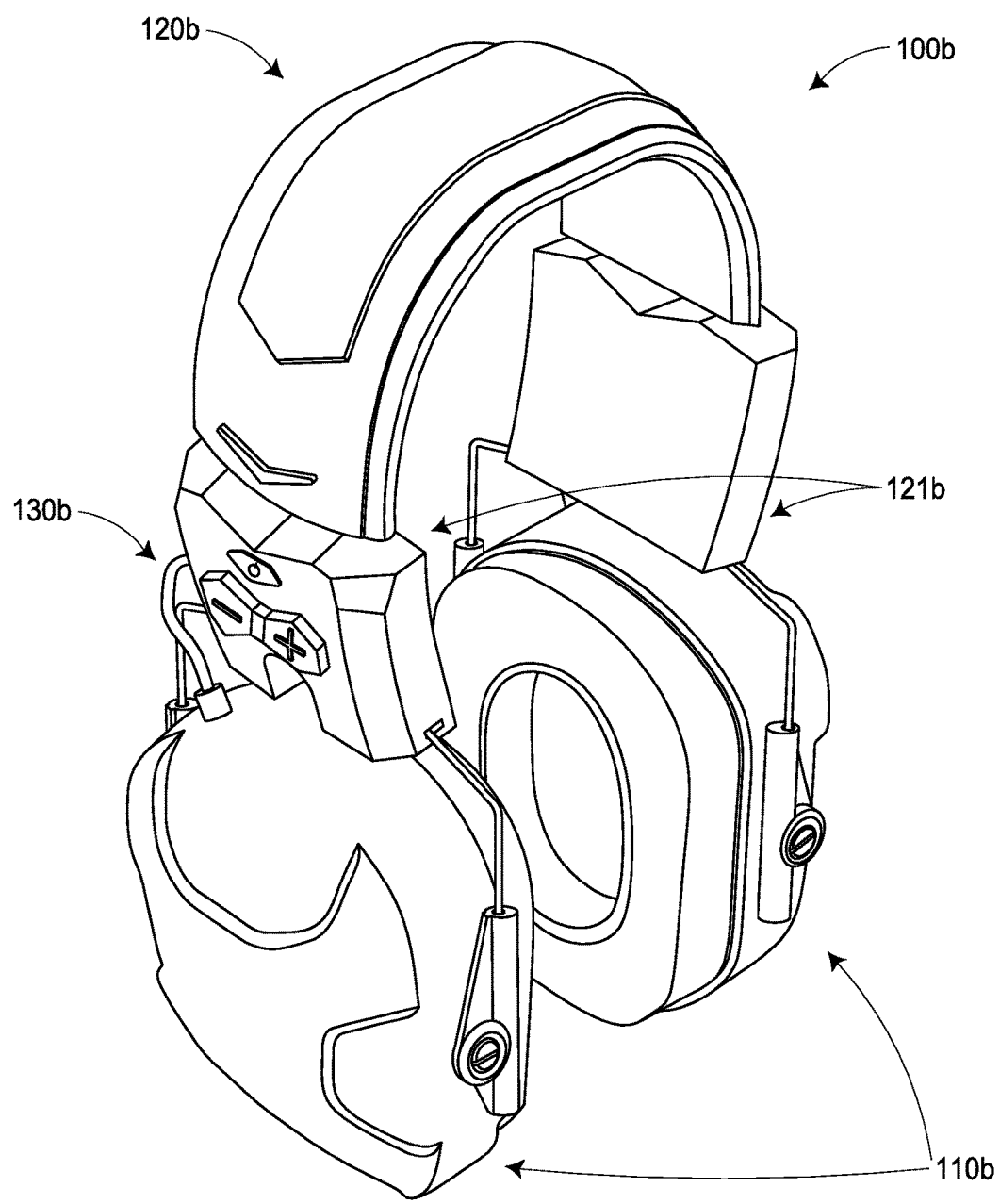
FIG. 3B is another perspective view of the electronic ear protection device of FIG. 3A.
Figure 3C:
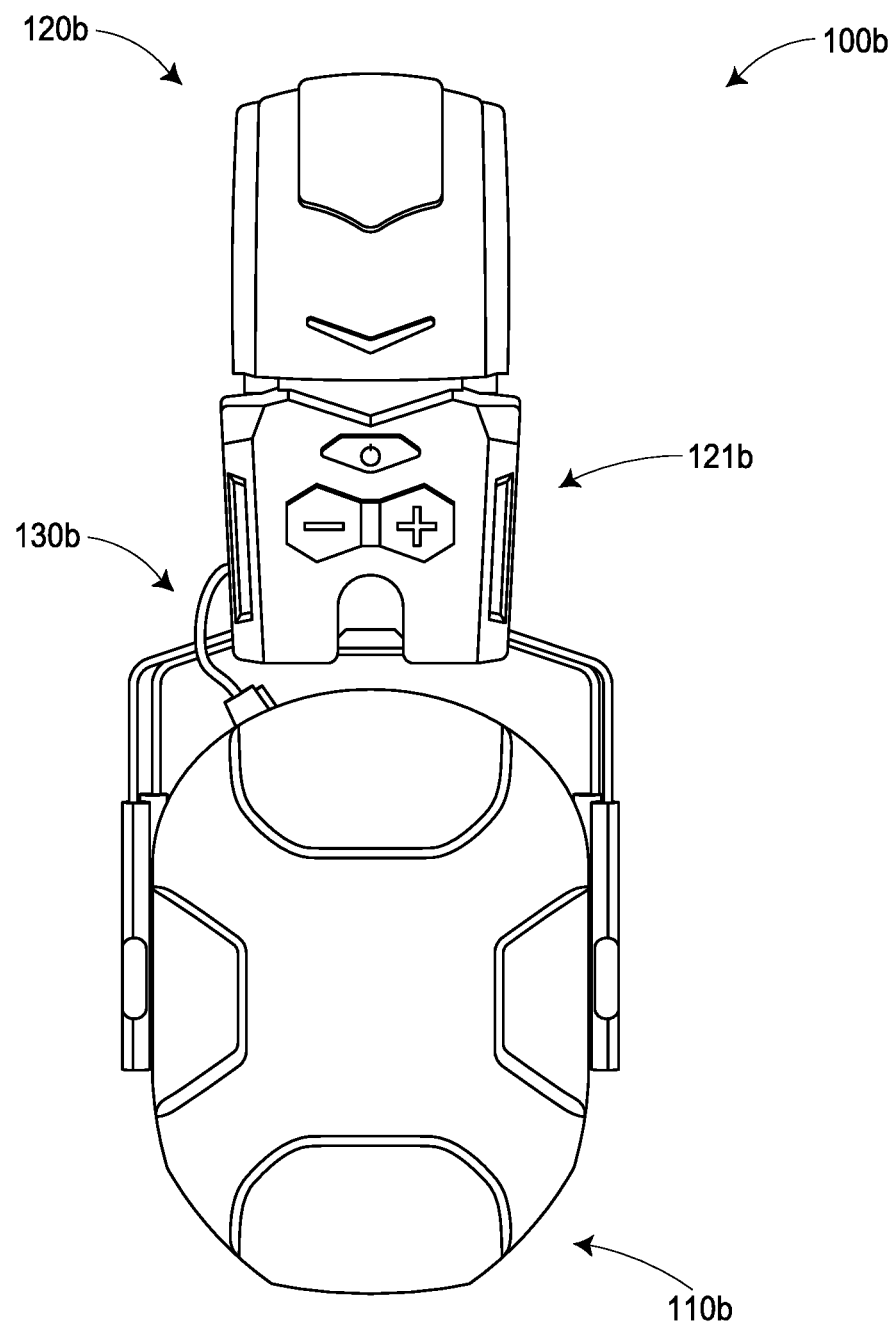
FIG. 3C is a side view of the electronic ear protection device of FIG. 3A.
Figure 3D:
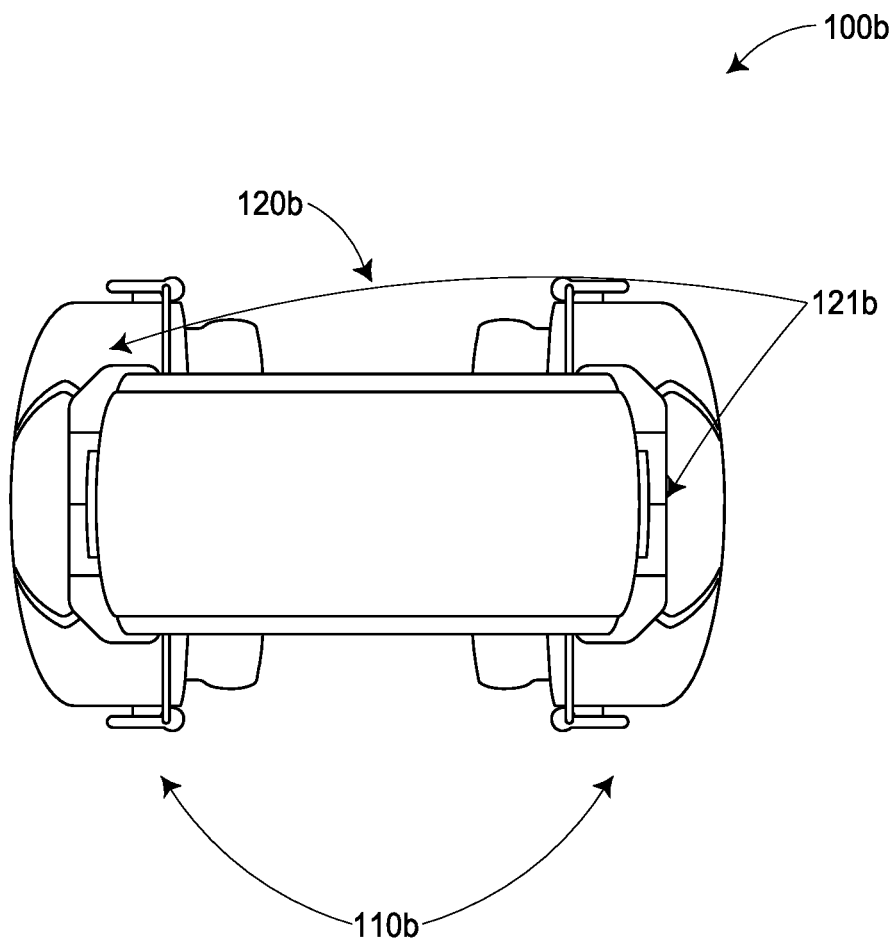
FIG. 3D is a top view of the electronic ear protection device of FIG. 3A.
Figure 3E:
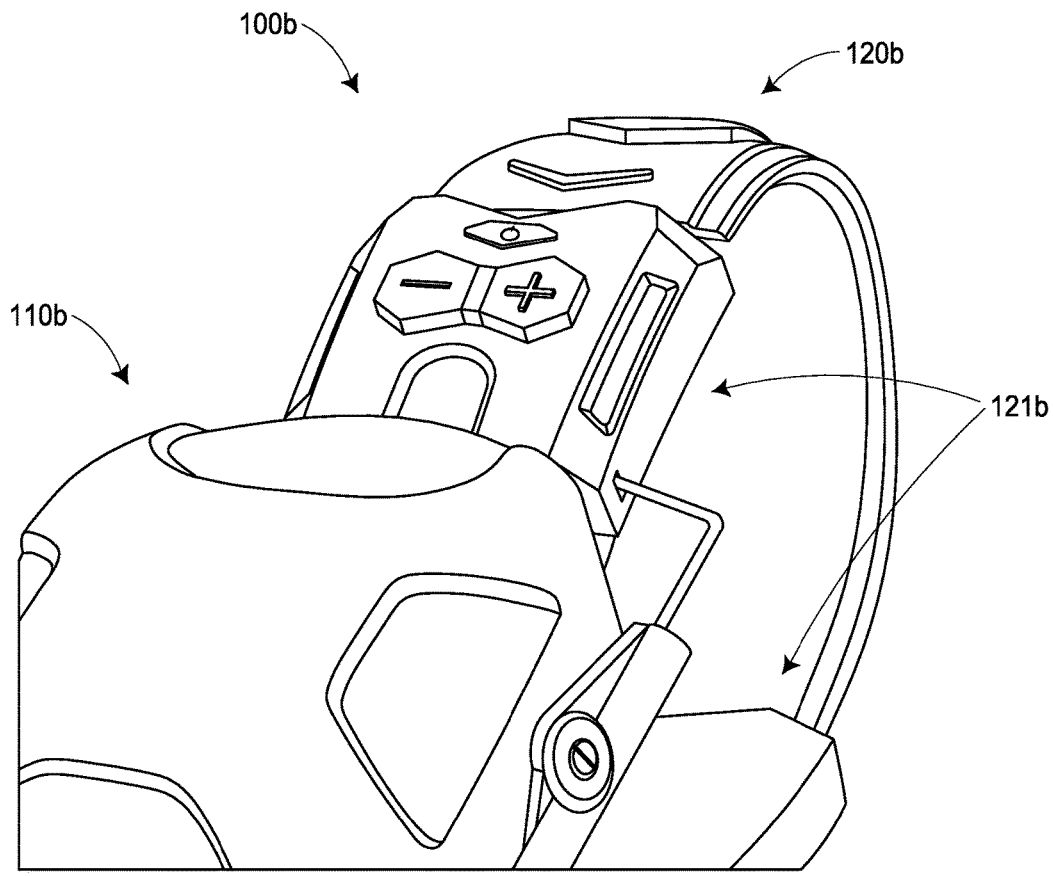
FIG. 3E is another perspective view of a portion of the electronic ear protection device of FIG. 3A.
Figure 3F:
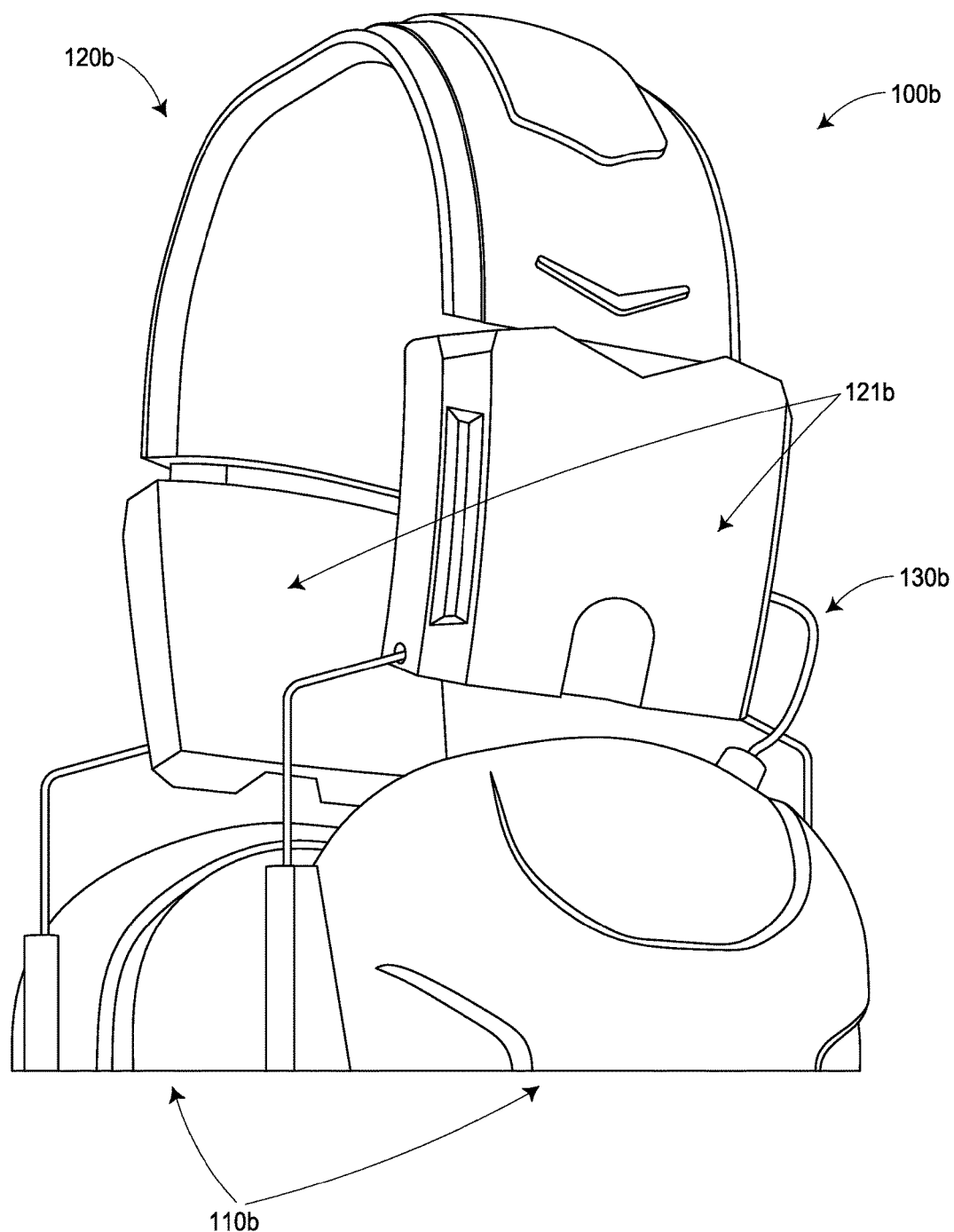
FIG. 3F is another perspective view of a portion of the electronic ear protection device of FIG. 3A.
Figure 3G:
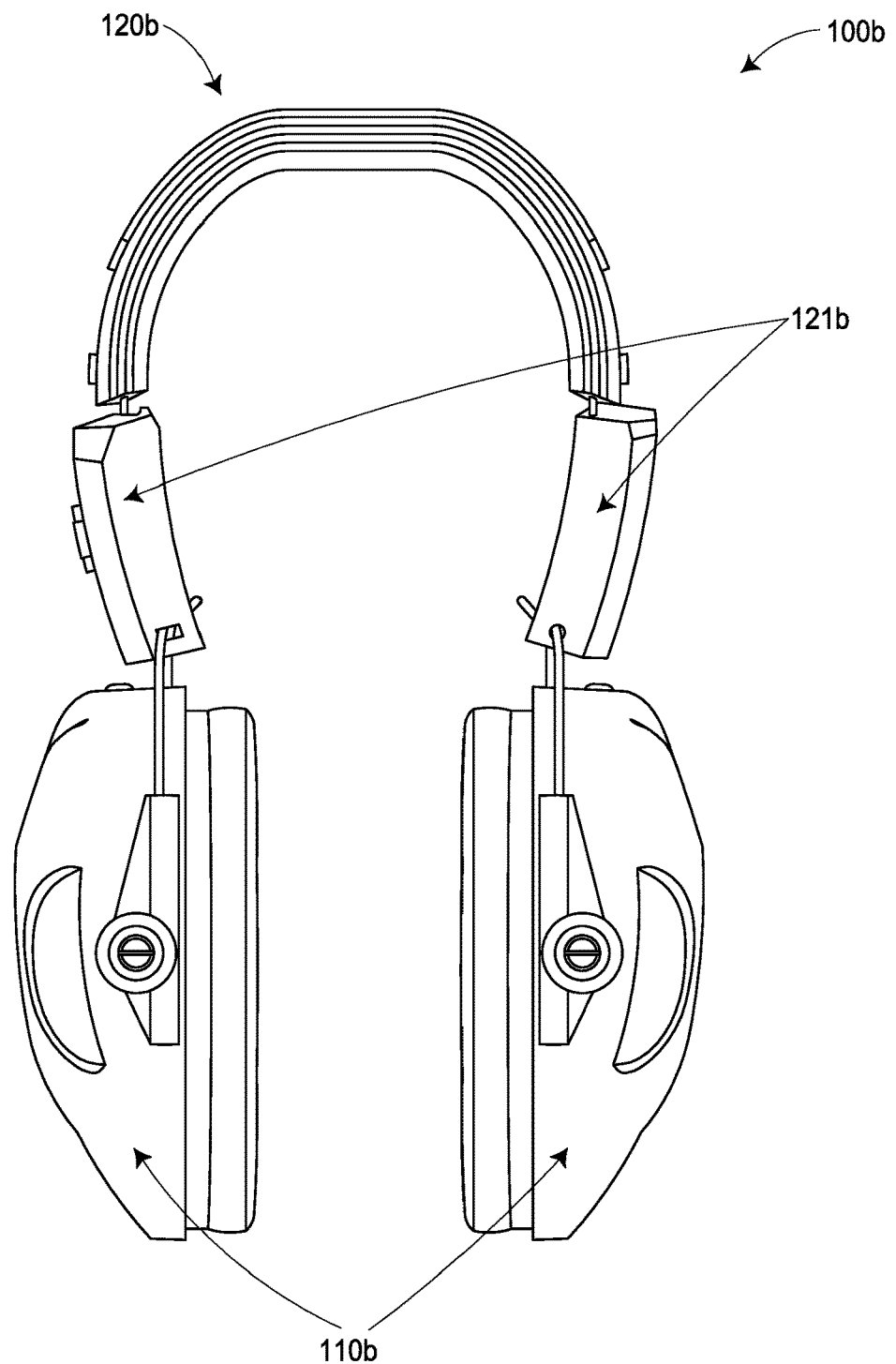
FIG. 3G is a front view of a portion of the electronic ear protection device of FIG. 3A.

In some embodiments, the sound control module 121 and the microphone 123 may be designed as a separate structure located on the surface of the outer shell of the ear cups 110. FIG. 2 illustrates a partial schematic view of such an embodiment of an electronic ear protection device 100*a* having a headband 120*a*; ear cups 110*a* each having an ear pad 111*a* and an outer shell 115*a*; and an electronic sound control module 121*a* on the surface of the outer shell 115*a* of the ear cups 110*a*. Each of the device 100*a*, the headband 120*a*, the ear cups 110*a*, the ear pad 111*a*, the outer shell 115*a*, and the module 121*a* are constructed similar to the device 100, the headband 120, the ear cups 110, the ear pad 111, the outer shell 115, and the module 121 shown in FIG. 1, respectively, except the location of the module relative to the device. The module 121*a* may contain one or microphone (not shown) and associated electronics as the module 121 described in relation with FIG. 1.

Turning back to FIG. 1, in the illustrated embodiment, the electronic sound control module 121 contains one or more control buttons 122. In some embodiments, the module 121 may additionally or alternatively contain componentry enabling connection to external audio sources. For example, the module 121 may include audio input port such as a 3.5 mm analog input jack for a wired connection, or a BLUETOOTH® chipset for a wireless connection. In some embodiments, the one or more buttons 122 optionally provide a user of the device 100 with control over the volume of ambient sound. The buttons 122 may be pressed to control volume of ambient sounds captured by the microphone 123. In still another embodiment, the one or more buttons 122 can allow the user to adjust some other or additional function of the headset 100 (e.g. sound threshold level above which sound is filtered by the electronics of the headset).

In the illustrated embodiment, the one or more buttons 122 include three buttons, which are a volume up button, a volume down button, and a power button. However, in some embodiments, buttons 122 may have fewer or more buttons (e.g., two, four, five or more than five buttons) for additional control. Buttons 122 may be designed to be activated by various mechanisms, for example, by pressing, or by touching (e.g., capacitive touch sensor). Although the illustrated embodiment uses button interfaces implemented on the device 100, the teachings herein are applicable to devices controlled in a wide variety of ways. For example, a user may control the device using one or more user interfaces on the device, including but not limited to, buttons, switches, knobs, levers, slides, touch screens, and/or other controls.

In some embodiments, one or more of the module 121, buttons 122 and/or microphone 123 can optionally be on both the left and right side of the headband 120, such that the volume of ambient sounds can be separately controlled to the left and right ears. In another embodiment, where the module 121 is on both the right and left side of the headband 120, the user can adjust the volume in both ear cups 110 via either of the modules 121, providing increased flexibility to the user in operating the device 100. In one embodiment, the module(s) 121 can optionally include two or more microphones, which can advantageously aid in capturing sounds at a wide variety of angles, including, for instance, 360 degrees around a user. Thus, while the microphones can be used to detect the same sounds, each microphone can face a different direction (e.g., at 90 degrees to each other, at 180 degrees to each other, etc.) and provide a more accurate detection of the noise. For example, the microphones closer to the right of the user can detect noise coming from the right, and the microphones closer to the left of the user can detect the noise coming from the left. The sounds can be reproduced to the speaker(s) of each or ear cups 110 such that the user can better discriminate which direction sounds are coming from. For instance, if a turkey gobbles to the right of the user, the right-side speaker would reproduce the sound at a higher volume level relative to the left-side speaker.

For example, FIGS. 3A-3G show one embodiment of an ear protection device 100b having two sound control modules 121b, one corresponding to each ear piece 110b, where each module 121b has its own microphone and sound processing electronics. In particular, the illustrated electronic ear protection device 100b includes two electronic sound control modules 121b, two ear cups 110b, a headband 120b, and wirings 130b electronically connecting modules 121b with speakers within ear cups 110b. In the illustrated embodiment, while both sound control modules 121b include their own microphones and sound processing electronics (not shown), only one sound control module 121b contains a control interface. In particular, the illustrated control interface includes volume up, volume down, and power buttons, providing common control of the volume and power for both ear cups. A wire runs through the headband 120b to communicate power, volume, or depending on the embodiment, additional signals (e.g., a received BLUETOOTH® audio stream) from the sound control module 121b including the control interface to the other module 121b. In alternative embodiments, each module 121b can include its own control interface, allowing independent control (e.g., volume, power, frequency, BLUETOOTH®, etc.) for each ear cup 110b. Each of the device 100b, the headband 120b, the ear cups 110b, and the module 121b can include internal componentry similar to any of the other embodiments described herein, such as those shown and described with respect to FIGS. 1 and 3.

Although the illustrated embodiment includes one speaker in each ear cup, other implementations are possible. In one example, separate speakers are provided for sound captured from each microphone of the device. Thus, if a sound is generated behind and to the right of the user, a corresponding speaker would play the sound the loudest.

In some embodiments, the electronic sound control module 121 and other electronic compartments may be designed to be turned off automatically, for example, after lack of the activity user for certain length of time.

Figure 4:
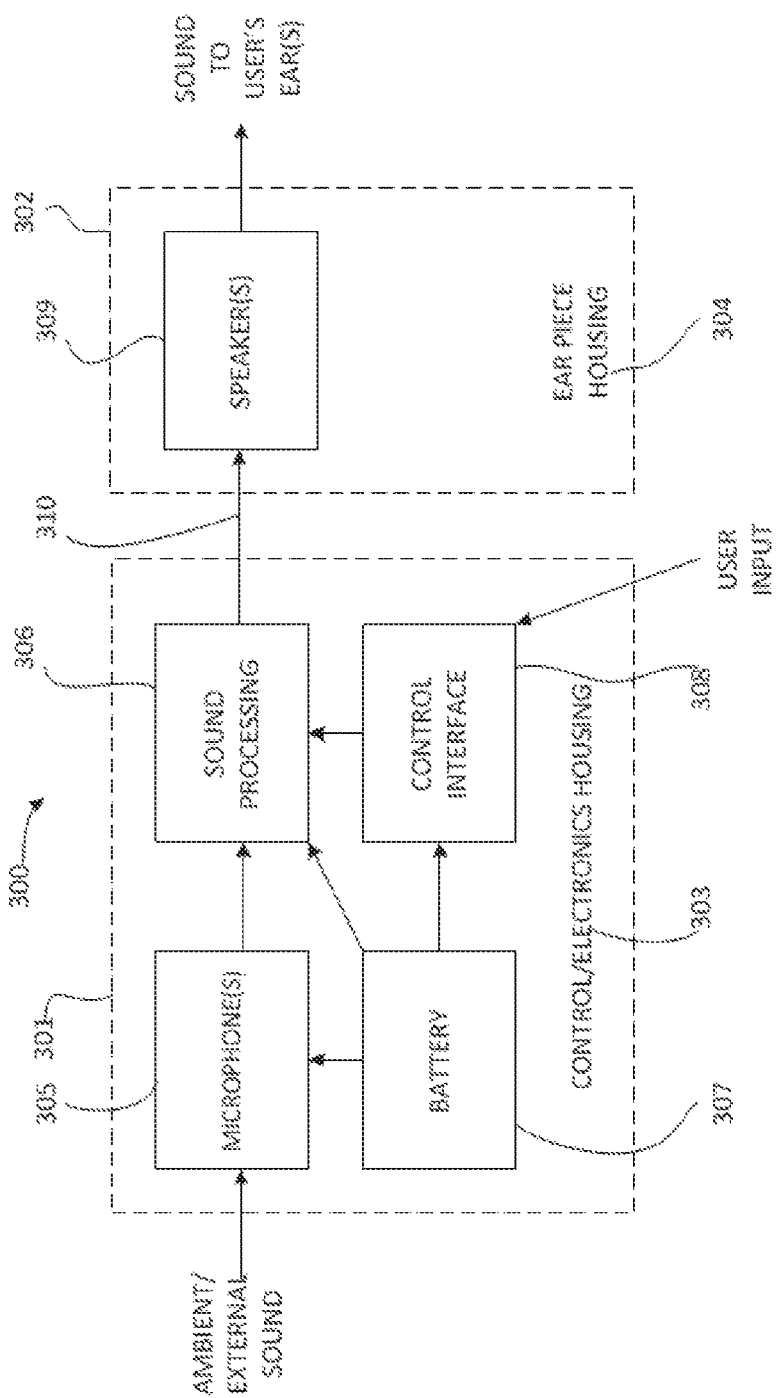
FIG. 4 is a schematic block diagram of an electronic ear protection device according to one embodiment.

FIG. 4 is a schematic block diagram of an electronic ear protection device 300 according to one embodiment. The electronic ear protection device 300 includes at least one electronic sound control module 301 encased by or otherwise supported by a control/electronics housing 303; ear cups 302 each encased by or otherwise supported by an ear piece housing 304; and wiring 310 or some other wireless or wired communication link, which electrically connects the module 301 and the ear cups 302. In some embodiments, the module 301 may optionally be located on/at a portion of a headband of the ear protection device, for example, such as the module 121 on the headband 120 as described in relation to FIG. 1. In another embodiment, the module 301 may optionally be located at other locations, for example, on/at the ear cups 302, such as the module 121 on the ear cups 110 as described in relation to FIG. 2. The module 301 includes one or more microphone(s) 305, a sound processing unit 306 and a control interface 308, which are powered by a battery 307 or any other suitable power sources. A battery may be additionally or alternatively included in ear cups 302. The ear cups 302 include one or more speaker(s) 309. When ambient or external sound is detected by the microphone(s) 305, the signal captured by the microphone(s) 305 is processed by the sound processing unit 306. The sound processing is also controlled by signal from the control interface 308 generated by user input. The signal processed by sound processing unit 306 is subsequently conducted via wiring 310 to speaker(s) 309 within the ear cups 302. The received signal drives the speaker(s) 309, which produces sound to the user's ear(s).

The module 301 and/or ear cups 302 may include software, firmware, circuitry or other hardware, or some combination thereof suitable for the implementing the corresponding functionality described herein. For example, the module 301 can include at least one processor which executes software or firmware to implement the sound processing unit 306. Sound processing can be implemented via a wide variety of functions, including amplification, equalization, echo suppression or cancellation, compensation for multipath acoustic effects, noise cancellation, wind reduction, and/or other processing described in this section or elsewhere in this specification.

Figure 5A:
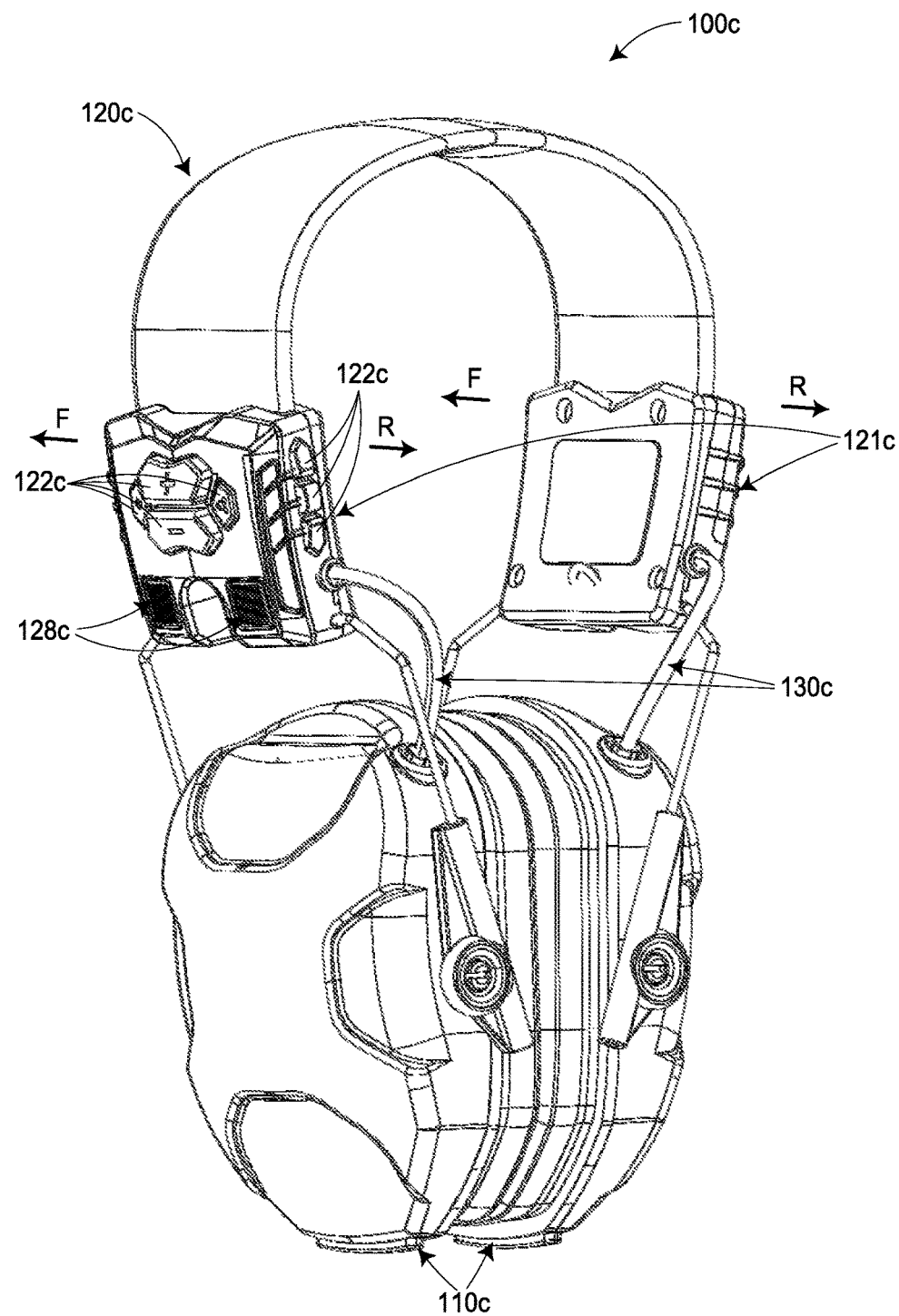
FIG. 5A is a perspective view of an electronic ear protection device according to one embodiment.
Figure 5B:
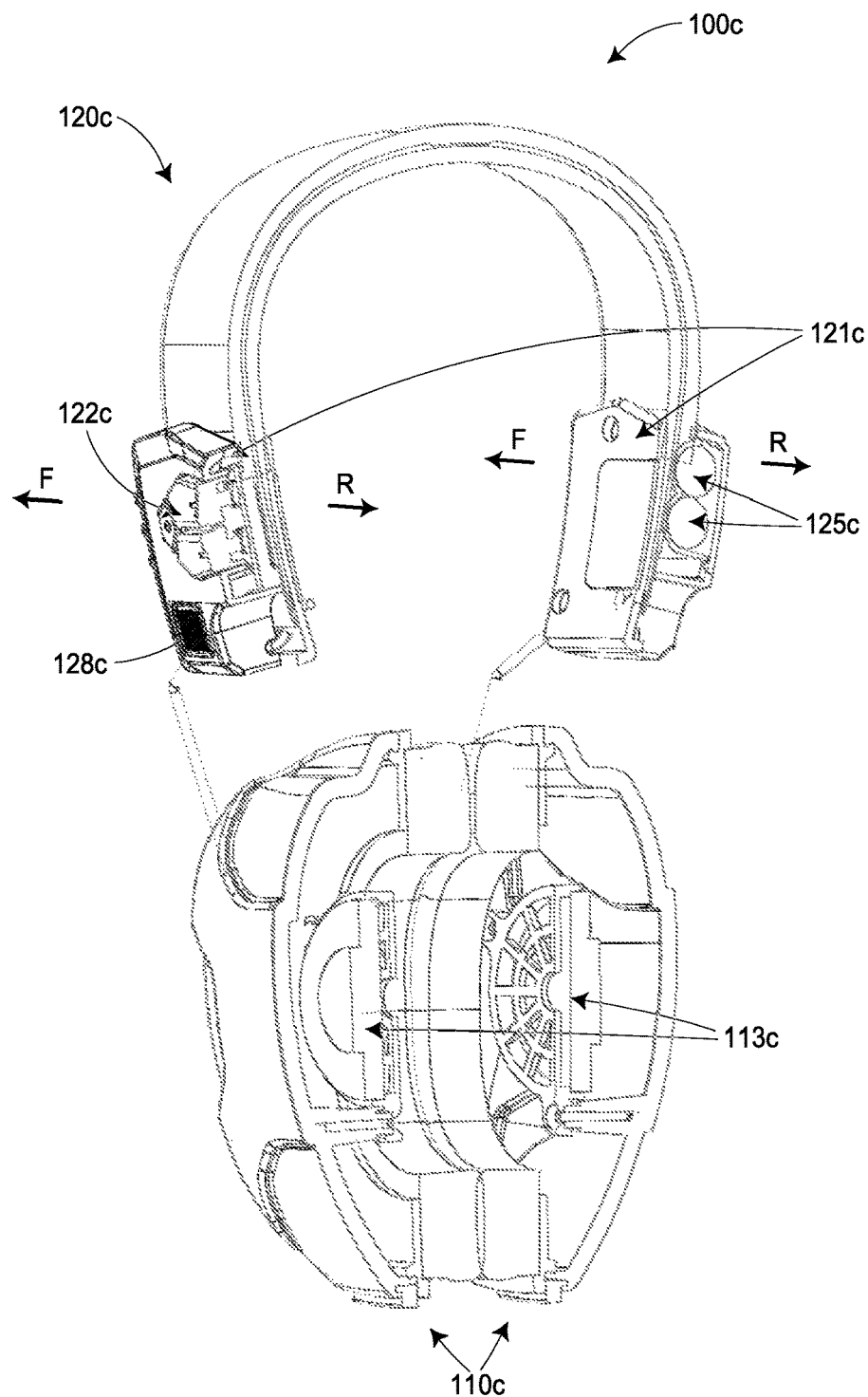
FIG. 5B is a partial cross-sectional view of the electronic ear protection device of FIG. 5A.
Figure 5C:
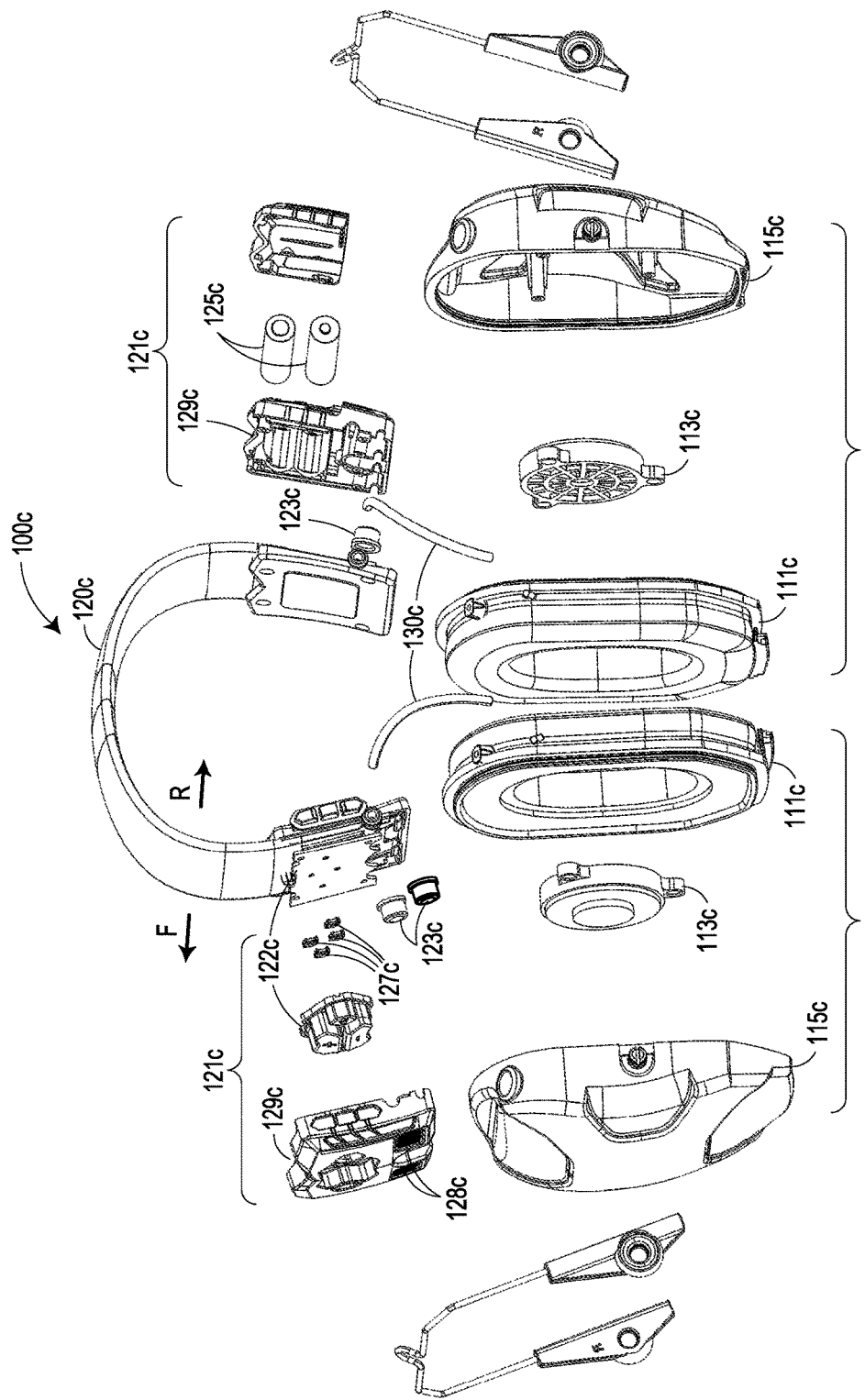
FIG. 5C is an exploded view of the electronic ear protection device of FIG. 5A.

FIGS. 5A-C show one embodiment of an ear protection device 100c. FIG. 5A is a perspective view of the ear protection device 100c, and FIGS. 5B-C are cross-sectional view and exploded view of the ear protection device 100c, respectively, showing some of its internal components. The ear protection device 100c is similar to the ear protection device 100b described in relation to FIGS. 3A-G or the ear protection device 300 described in relation to FIG. 4, and each components of the ear protection device 100c is constructed similar to the ear protection device 100b or 300 except as noted below.

As shown in FIGS. 5A-C, the illustrated embodiment of the ear protection device 100c includes two electronic sound control modules 121c, two ear cups 110c, a headband 120c, and wirings 130c electronically connecting modules 121c with speakers 113c. Each of the speakers 113c is disposed or housed in one of the ear cups 110c between an outer shell 115c and a pad 111c. A wire (not shown) runs through the headband 120c to optionally communicate one or more of power, volume, or additional signals (e.g., a received BLUETOOTH® audio stream) from one sound control module 121c (e.g., the control module 121c that includes the control interface) to the other module 121c. In alternative embodiments, each module 121c can optionally include its own control interface, allowing independent control (e.g., volume, power, frequency, BLUETOOTH®, etc.) for each ear cup 110c. Each of the headband 120c, the ear cups 110c, and the module 121c can include internal componentry similar to any of the other embodiments described herein, such as those shown and described with respect to FIGS. 1, 3 and 4.

The illustrated control interface of the control module 121c includes one or more buttons 122c. As shown in FIG. 5C, the control module 121c may further include input sensors 127c positioned under the one or more buttons 122c to receive user input from the user pressing on the buttons 122c. In the illustrated embodiment, the buttons 122c include four buttons on the main surface of the control module 121c, and three buttons on the side wall of the control module 121c. The four buttons on the main surface of the control module 121c may be volume up, volume down, power, and an additional button. In some embodiments, the control interface may include two, three, four, five, six, eight or more buttons. In some embodiments, the buttons 122c may include a BLUETOOTH® on/off or a BLUETOOTH® pairing button. In some embodiments, the buttons 122c may include one or more buttons which enable the user to toggle between multiple functions/modes of the ear protection device described in this section or elsewhere in the specification. Even though the illustrated control interface of the control module 121c includes push buttons, as described above, the control interface buttons 122c may be designed to be activated by various mechanisms, for example, by pressing, or by touching (e.g., capacitive touch sensor). In some embodiments, the control interface may include switches, knobs, levers, slides, touch screens, and/or other controls.

As shown in FIGS. 5B-C, in the illustrated embodiment, both of the sound control modules 121c optionally include their own microphones 123c and sound processing electronics (not shown) within sound control module housings 129c. Optionally, each of the sound control modules 121c includes two microphones 123c, one microphone placed near the front side (marked "F" in FIGS. 5A-C) and the other microphone placed near the rear side (marked "R" in FIGS. 5A-C) of each sound control modules 121c, respectively, such as shown in FIG. 5C. However, in alternative embodiments, each of the sound control modules 121c may optionally include one, three, or more than three microphones. As discussed above, including more microphones may advantageously aid in capturing sounds at a wide variety of angles, including, for instance, 360 degrees around a user. In some embodiments, only one of the sound control modules 121c may include microphones. The microphones 123c may be dynamic microphones, condenser microphones or any type of microphones suitable for capturing sound (e.g., capturing ambient sound). In the illustrated embodiment, the sound control module housings 129c include microphone openings 128c covered with mesh, such that the openings allow sound to pass through it toward the microphones 123c while protecting the microphones 123c from the environment. In alternative embodiments, the openings 128c may be simple orifices or include sponge to protect the microphones 123c.

As described in relation to FIG. 4, ear protection devices may include a power source or batteries. As shown in FIGS. 5B-C, the illustrated embodiment of the ear protection device 100c includes batteries 125c within the sound control module housing 129c of one of the sound control modules 121c which does not include the buttons 122c. In the illustrated embodiments, the batteries 125c are cylindrical (such as AA or AAA batteries), but in alternative embodiments, the batteries 125c may be rectangular (such as 9-volt batteries) or coin-shaped. In some embodiments, the batteries 125c may be primary cells. The housing 129c encasing the batteries 125c may include a removable lid for the easy access to the battery compartment as illustrated in FIG. 5C, such that the batteries 125c can be easily replaced without disassembling the entire housing 129c. In some embodiments, the batteries 125c may be rechargeable batteries, for example, such as lithium ion, lithium ion polymer batteries. In further embodiments, the ear protection device 100c may be designed such that the batteries 129c can be recharged without removing them, for example, by including a slot to receive a cable connector (e.g., USB, micro-USB) to which a charger can be coupled. In some embodiments, the batteries 125c may be additionally or alternatively included in the ear cups 110c.

Although examples of components and functionality are shown in FIGS. 1-5, an electronic ear protection device can include more or fewer features. Moreover, an electronic ear protection device can be implemented using a wide variety of form factors, including any of the form factors shown and described herein (e.g., with respect to FIGS. 1-5) or another form factor.

Terminology

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. Conjunctions, such as "and," "or" are used interchangeably and are intended to encompass any one element, combination, or entirety of elements to which the conjunction refers.

Depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially.

The multi-source audio amplification and ear protection devices described herein may comprise software, firmware, hardware, or any combination(s) of software, firmware, or hardware suitable for the purposes described herein. Various disclosed and illustrated modules may be implemented as software and/or firmware on a logic circuitry, processor, microcontroller, ASIC/FPGA, or dedicated hardware. Software and other modules may reside remotely from a multi-source audio amplification and ear protection device, such as on personal computers, computerized tablets, PDAs, and other devices suitable for the purposes described herein, such as remote control of a multi-source audio amplification and ear protection device. Software and other modules may be accessible via local memory, via a network, or via other means suitable for the purposes described herein. User interface components described herein may comprise buttons, knobs, dials, switches, touchscreen interfaces, and other suitable interfaces.

Computer program instructions may be stored in a computer-readable memory that can direct a computer or other programmable data processing apparatus to operate in a particular manner, thereby aiding in controlling a multi-source audio amplification and ear protection device.

The processing of the various components of the illustrated systems can be distributed across multiple logic circuits, processors, and other computing resources. In addition, two or more components of a system can be combined into fewer components. Various components of the illustrated systems can be implemented in one or more virtual machines, rather than in dedicated computer hardware systems. Moreover, in some embodiments the connections between the components shown represent possible paths of data flow, rather than actual connections between hardware. While some examples of possible connections are shown, any of the subset of the components shown can communicate with any other subset of components in various implementations.

While certain embodiments of the inventions have been described, these embodiments have been presented by way of example only, and are not intended to limit the scope of the disclosure. Therefore, the concepts described herein can be applicable to a variety of users and are not limited to certain uses. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally,"

and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. An electronic ear protection device, comprising:
   a pair of ear cups, each having a speaker therein;
   a headband positioned above the pair or ear cups; and
   a pair of arms that connect the pair of ear cups to opposite ends of the headband; and
   an electronic sound control module attached to the headband, the module comprising:
      one or more microphones configured to detect an ambient sound and generate a corresponding ambient sound signal,
      one or more inputs operable to control a volume of the ambient sound signal delivered to the speakers in the ear cups via one or more cables that extend from the electronic sound control module to the speakers, and
      circuitry operable to process the ambient sound signal and to communicate the processed ambient sound signal to the speakers in the ear cups via the one or more cables,
   wherein a user can actuate the one or more inputs of the electronic sound control module attached to the headband to thereby control the volume of ambient sound provided to the user through the speakers in the ear cups.

2. The device of claim 1, wherein the circuitry is configured to provide different amounts of amplification to certain frequencies relative to other frequencies when processing the ambient sound signal.

3. The device of claim 1, wherein the circuitry is configured to filter out the ambient sound signal having a decibel level greater than a predetermined decibel level.

4. The device of claim 1, wherein the one or more inputs comprise one or more buttons.

5. The device of claim 1, wherein a user can actuate the one or more inputs to thereby turn the power of the circuitry on or off.

6. The device of claim 1, wherein the electronic sound control module comprises a first unit attached to a first end of the headband and a second unit attached to a second end of the headband opposite the first end of the headband, wherein the first unit includes the one or more inputs.

7. The device of claim 6, wherein the second unit comprises one or more batteries housed therein.

8. The device of claim 6, wherein the first unit comprises a first microphone operable to detect the ambient sound from a first direction, and the second unit comprises a second microphone operable to detect the ambient sound from a second direction different from the first direction.

9. The device of claim 8, wherein the circuitry is configured to control sound output to the speaker of one of the pair or ear cups based on ambient sound captured by the first microphone and to separately control sound output to the speaker of the other of the pair of ear cups based on ambient sound captured by the second microphone.

10. The device of claim 1, wherein the electronic sound control module further comprises an electronic sound control module housing, wherein the housing houses the circuitry and the one or more microphones therein.

11. The device of claim 1, wherein the electronic sound control module attached to the headband is in communication with the speaker in each of the pair of ear cups via one or more wires.

12. An electronic ear protection device, comprising:
    a pair of ear cups, each comprising a speaker therein and an outer shell enclosing the ear cup, wherein the outer shell does not contain any exposed openings;
    a headband that interconnects and supports the pair of ear cups on opposite ends of the headband; and
    an electronic sound control module disposed outside of the ear cups, the module comprising
       one or more microphones configured to detect an ambient sound and generate a corresponding ambient sound signal,
       one or more user interface actuatable by a user to control a volume of the ambient sound signal delivered to the speakers in the ear cups, and
       circuitry configured to process the ambient sound signal and to communicate the processed ambient sound signal to the speakers in the ear cups.

13. The device of claim 12, wherein the electronic sound control module is coupled to at least one end of the headband and electrically connected to the speakers in the ear cups via a connector between the headband and the ear cups.

14. The device of claim 12, wherein the electronic sound control module comprises a first unit attached to a first end of the headband and a second unit attached to a second end of the headband opposite the first end of the headband, wherein the first unit includes the one or more inputs.

15. The device of claim 14, wherein the second unit comprises one or more batteries housed therein.

16. The device of claim 12, wherein the circuitry is configured to filter out audio above a threshold decibel level.

17. The device of claim 12, wherein the one or more user interface comprises one or more buttons actuatable by the user.

18. The device of claim 12, wherein the one or more microphones comprises a first microphone operable to capture ambient sound from a first direction, and a second microphone configured to capture ambient sound from a second direction different from the first direction.

19. The device of claim 18, wherein the circuitry is configured to control sound output to the speaker of one of the pair or ear cups based on ambient sound captured by the first microphone and to separately control sound output to the speaker of the other of the pair of ear cups based on ambient sound captured by the second microphone.

20. The device of claim 12, wherein the circuitry provides frequency-dependent amplification to at least the ambient sound signal.

21. The device of claim 12, wherein the electronic sound control module disposed outside of the ear cups is in communication with the speaker in each of the pair of ear cups via one or more wires.

* * * * *